United States Patent [19]

Hashimoto et al.

[11] 4,350,665

[45] Sep. 21, 1982

[54] CATALYTIC REACTOR

[75] Inventors: Noboru Hashimoto, Yokohama; Mitsu Akatsu, Kawasaki, both of Japan

[73] Assignee: JGC Corporation, Tokyo, Japan

[21] Appl. No.: 205,158

[22] Filed: Nov. 10, 1980

[30] Foreign Application Priority Data

Nov. 8, 1979 [JP] Japan .............................. 54-144835

[51] Int. Cl.³ .......................... B01J 8/04; B01J 12/00; B01J 19/24
[52] U.S. Cl. .................................. 422/191; 422/194; 422/195; 422/207; 422/220
[58] Field of Search .......................... 422/191–195, 422/207; 261/114 VT, 114 TC

[56] References Cited

U.S. PATENT DOCUMENTS

| | | | |
|---|---|---|---|
| 2,104,858 | 1/1938 | Ferguson | 422/191 X |
| 2,632,692 | 3/1953 | Korin et al. | 422/194 |
| 2,747,973 | 5/1956 | Hinrichs | 422/195 X |
| 3,235,344 | 2/1966 | Dreyer et al. | 422/191 |
| 3,498,755 | 3/1970 | Borre | 422/194 X |
| 3,541,000 | 11/1970 | Hanson et al. | 422/194 X |
| 3,592,613 | 7/1971 | Boyd | 422/191 |
| 3,723,072 | 3/1973 | Carson et al. | 422/194 |
| 3,787,189 | 1/1974 | Muffat et al. | 422/194 |
| 3,977,834 | 8/1976 | Alcock et al. | 422/194 |
| 4,235,847 | 11/1980 | Scott | 422/220 |

Primary Examiner—Bradley Garris
Attorney, Agent, or Firm—Armstrong, Nikaido, Marmelstein & Kubovcik

[57] ABSTRACT

Mixing of gases in a catalytic reactor having plural beds of packed catalyst which are disposed in series along the direction of the reactant gas flow is improved by providing a gas-mixing means in a space prepared between each bed, said means being composed of a separator plate mounted vertically on the rear face of a grating apparatus for supporting catalyst bed for partitioning the upper part of said space, a gas-distributor tube for providing a gas to-be-mixed with the aforesaid reactant gas and a gas-dispersing board located under said tube for establishing the complete gas mixing.

The typical application of this invention will be found in the reactor for catalytic dehydrogenation of ethylbenzene to produce styrene.

9 Claims, 22 Drawing Figures

CATALYTIC REACTOR

BACKGROUND OF THE INVENTION

1. Field of the Invention

The present invention relates to a fixed-bed type catalytic reactor, particularly, to an improvement in gas-mixing apparatus in the reactor for catalytic reaction of gases.

2. State of the Art

In some chemical processes in which a catalytic reaction in gas-phase occurs by letting a reactant gas pass through two to three or more catalyst beds disposed in series along the direction of the gas flow in a reactor vessel, it is often required to mix a gas or gas-mixture which passed through a certain catalyst bed (hereinafter referred to as "the first gas") with another gas or gas-mixture (hereinafter referred to as "the second gas") before introducing them into the next catalyst bed. Such processes may include the process for producing styrene by catalytic dehydrogenation of ethylbenzene, for example. Because the dehydrogenation reaction is endothermic, the gas temperature in the catalyst bed decreases as the gas passes through the catalyst bed, and hence, the dehydrogenation reaction does no longer proceed at a satisfactory rate in the next catalyst bed. Thus, it is necessary to blow high temperature steam as a heat source into the effluent gas from a catalyst bed to increase the gas temperature therein.

In order to achieve uniform progress of the reaction and a high conversion, it is desired that the steam blown in between the catalyst beds is mixed with the reactant gas to the highest extent of homogeneity. On the other hand, the reactor is preferably small, and therefore, it is desirable that the space between the catalyst beds, which is available for mixing of the first gas and the second gas, should be as small as possible.

To date, there has been made some efforts to harmonize the above desires. One example is blowing of the second gas in radial or centripetal directions into the first gas flowing in the direction of axis of the reactor, and another is simultaneous blowing out of the first and the second gas from nozzles provided in a double tube so as to mix the gases at the time of blowing. These methods are still dissatisfactory because of insufficient homogeneity of mixing or complexity of structure of the mixing apparatus resulting in disadvantages in construction and maintenance.

SUMMARY OF THE INVENTION

We have made an experimental study and reached one solution of the above problem.

The object of the present invention is to provide an improved fixed-bed type catalytic reactor which is relatively simple structure without large space between the catalyst beds, i.e., small sized reactor, but offers high homogeneity of gas mixing.

The reactor of the present invention has plural catalyst beds, wherein the first gas which passed through an upstream catalyst bed is mixed with the second gas before passing a downstream catalyst bed, and is characterized in that the reactor is provided with a gas-mixing apparatus which comprises at least one vertical separator plate installed on the rear face of a grating for supporting the upstream catalyst bed, a gas-distributor tube for the second gas having multiple nozzles installed rearward of the separator plate, and a gas-dispersing plate having multiple slits or perforations installed in the rearward side of the gas-distributor tube.

DRAWINGS

FIGS. 1, 2 and 3 show the fundamentals of an embodiment of the catalytic reactor according to the present invention.

FIGS. 4 and 5 show the details of an example of the gas-distributor tube.

FIGS. 11 and 12 show the percent of deviation of methane concentration at each sampling point shown in FIG. 10 from the mean methane concentration for the all sampling points.

DESCRIPTION OF THE PREFERRED EMBODIMENTS

Figure 1:
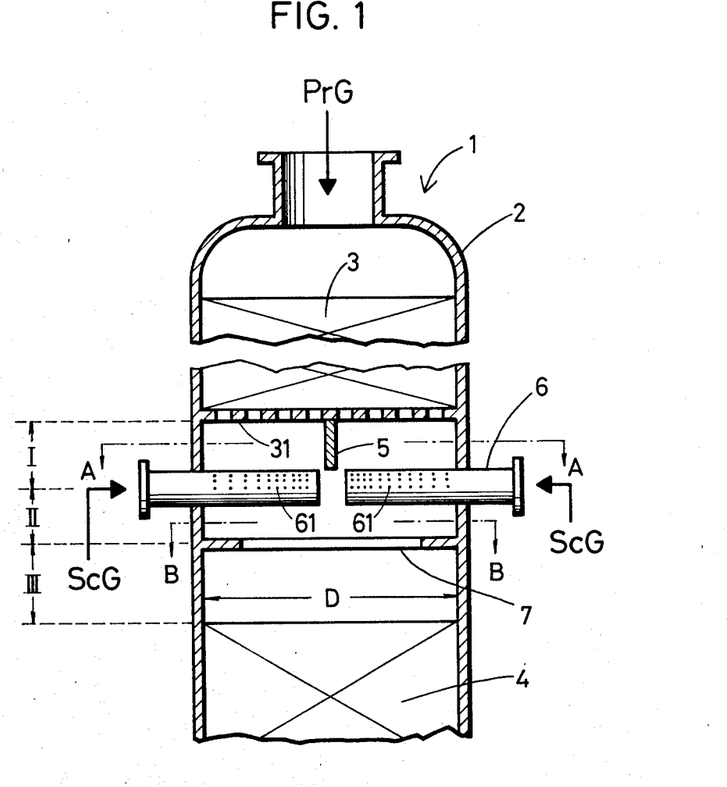
FIG. 1 is a longitudinal sectional view with partial omission.

With reference to the attached drawings, an embodiment of the present invention will be explained below:

The catalytic reactor 1 is constructed as a column type vessel 2, from the top of which the first gas PrG is introduced. While the first gas proceeds, after passing through the first catalyst bed 3 in the reactor to the second catalyst bed 4, it is divided into plural segments by the vertical separator plate 5, and the second gas ScG is blown thereinto in the perpendicular direction or slightly counter-currently to the stream of the first gas PrG through the multiple nozzles 61, 61,—provided in the gas-distributor tube 6 to cause preliminary mixing in each segment. Subsequently, the two gases are further mixed in the space under the gas-distributor tube, and then subjected to the final thorough mixing by the gas-dispersing plate 7.

The vertical separator plate 5 is mounted on the rear face of the grating for supporting the first catalyst bed 3 at the position on the diametrical center line of the grating. The space extending from the grating 31 to the central axis of the gas-distributor tube 6 is defined as the first mixing zone I, the height of which should be at least 0.18 time of the inner diameter D of the reactor. The distance from the grating to the upper part of the gas-distributor tube will be, though depending on the diameter of the tube, usually at least 0.14 time of the inner diameter D of the reactor. The separator plate 5 may not necessarily cover the entire height of the first mixing zone I, but will be effective if it has a height of at least ½ of the zone.

Figure 5:
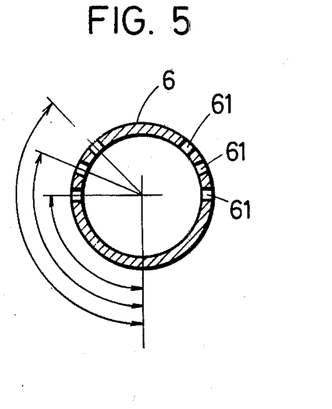
FIG. 5 is a cross-sectional view taken along lines C—C of FIG. 4.

The gas-blowing nozzles 61, 61,—of the gas-distributor tube 6 are preferably given in such directions that the blowing directions of the second gas ScG may be perpendicular (90°) to the direction of the first gas PrG, or counter currently in the angle range of 90° to 135°. In the example of FIG. 5, there are provided three rows of nozzles in the directions of 90°, 112.5° and 135°. A counter current blowing out in the directions above 135° was found to have a lower mixing effect. Further, in the case where the second gas is steam or something of a high temperature, direct blast of the high temperature gas to the grating is undesirable because the grating might be damaged by heat. The important point is to arrange the amounts of the second gas blowing out in each unit of the cross-sectional area of the column as uniformly as possible. For this purpose, it is useful to select a shape of the gas-distributor tube from various types of distributors as described below, and to regulate location, number or size of the nozzles.

The space extending from the central axis of the gas-distributor tube 6 to the gas-dispersing plate 7 is defined as the second mixing zone II. The height of the zone was found by experiments to be at least 0.06 time of the inner diameter D of the reactor.

Figure 2:
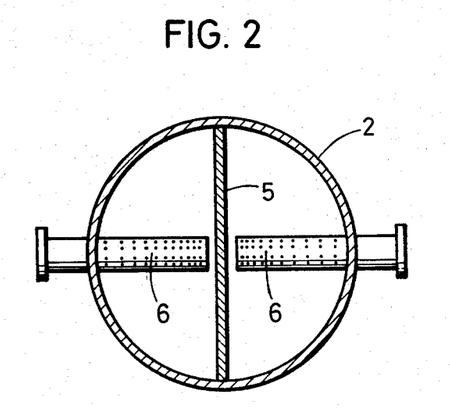
FIG. 2 is a cross-sectional view taken along lines A—A of FIG. 1.
Figure 3:
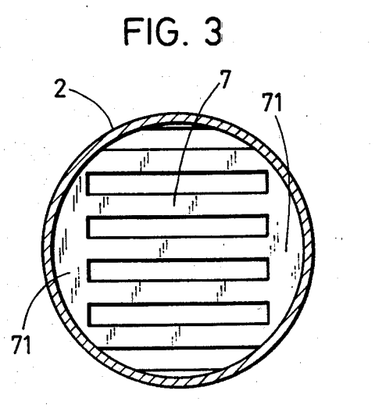
FIG. 3 is a cross-sectional view taken along lines B—B of FIG. 1.
Figure 4:
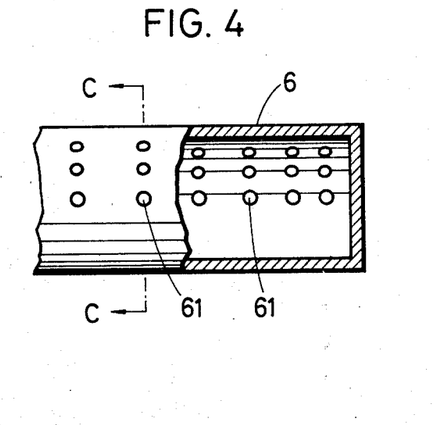
FIG. 4 is a side view with a partial cut-away to show the section.

The gas-dispersing plate 7 is chosen to be of such a shape that it causes the least pressure drop of the first gas PrG and the second gas ScG, and gives the best mixing thereof. In many embodiments, a suitable opening area ratio of the plate 7 for the column cross sectional area may be in the range of 35 to 60%. An opening area less than 35% causes too large pressure drop, and an opening area more than 60% gives insufficient mixing effect. In the case of using a plate provided with slitted openings, it is advantageous to arrange the slits in the direction approximately perpendicular to the direction of the second gas ScG blowing out from the gas-distributor tube 6, in other words, to arrange the slits to run parallel with the axis of the gas distributor tube. Also, in the case where the slitted plate is used in combination with a pair of gas-distributor tubes 6 inserted from the reactor wall in the radial direction thereof as shown in FIGS. 1 and 2, it is recommended to use a gas-dispersing plate having a semi-circle formed non-opening area 71, as shown in FIG. 3, at the location just under the fixing part of the second-gas-distributor tube to the reactor shell.

The space between the gas-dispersing plate 7 and the upper face of the second catalyst bed 4 is defined as the third mixing zone III, the height of which should be at least 0.12 time of the inner diameter D of the reactor.

The catalytic reactor according to the present invention achieves highly homogeneous mixing of gases by utilizing the above described gas-mixing apparatus. This is the most important merit which enables efficient catalytic reaction resulting in increased conversion of the reactants through the reactor. Further, it is possible to reduce the space between the catalyst beds required for the highly homogeneous mixing. The sum of the least heights of the above noted mixing zones I, II and III amounts to only 0.36 time of the inner diameter of the reactor. It has never been expected that satisfactory mixing could be performed in such a small space. Thus, the present invention realizes smaller-sized reactors.

As seen from the above description, the present invention includes various embodiments, which those skilled in the art could easily practice.

Figure 6A:
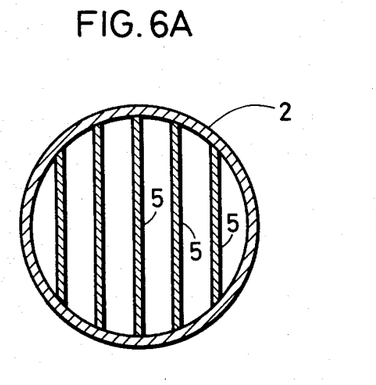
FIGS. 6A, 6B and 6C show a variety of embodiments of the vertical separator plate at the same cross sectional position as FIG. 2.
Figure 6B:
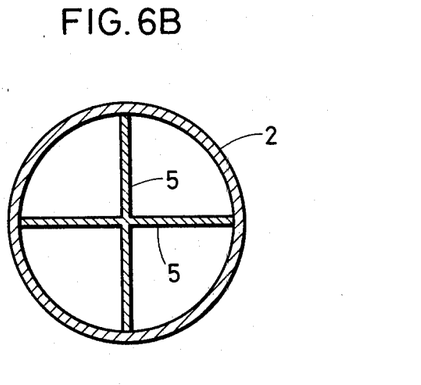
Figure 6C:
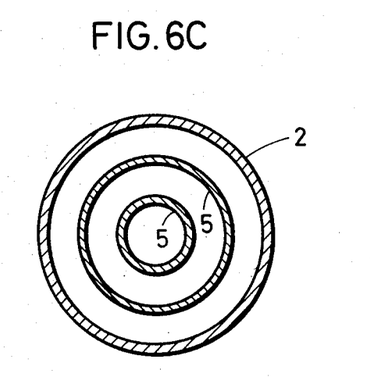

For example, the vertical separator plate 5 may be not only of the type as shown in FIGS. 1 and 2, the one plate being installed at the position including the diametrical center line of the vessel, but also of the types using plural parallel plates, crossing plates and cylindrically disposed plates concentrically to the reactor shell as shown in FIGS. 6A, 6B and 6C, respectively.

Figure 7A:
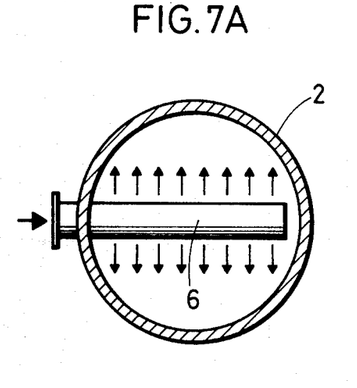
FIGS. 7A, 7B, 7C, 7D and 7E show various embodiments of the gas distributor tube at the same cross sectional position as FIG. 2, in which the vertical separator plate is omitted.
Figure 7B:
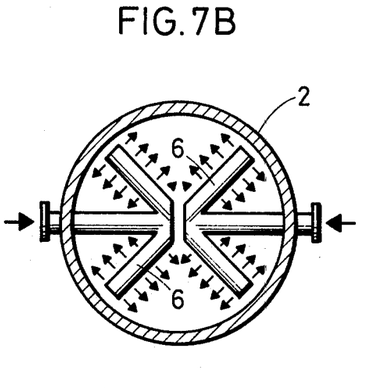
Figure 7C:
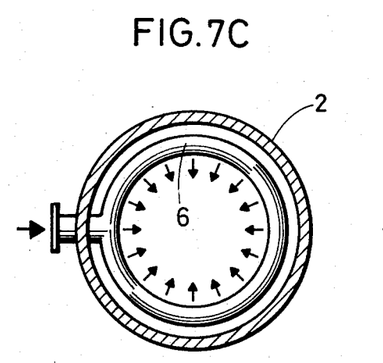
Figure 7D:
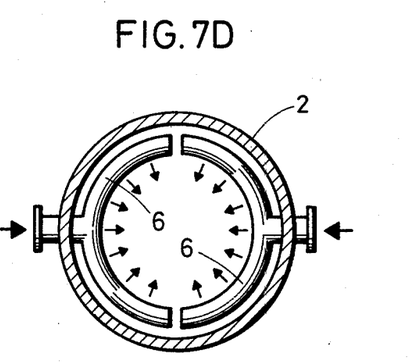
Figure 7E:
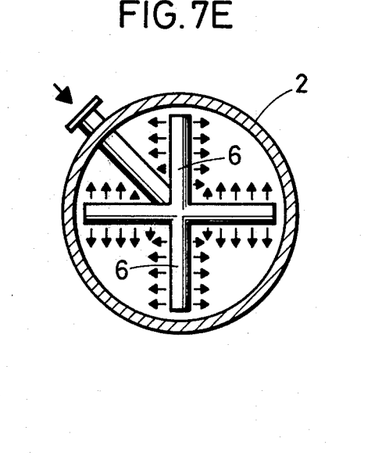

Also, the gas-distributor tube 6 may have the configurations, in addition to a pair of the confronting straight tubes as shown in FIGS. 1 and 2, more simply, of one tube as shown in FIG. 7A, or the arrow head type as shown in FIG. 7B and the cross type as shown in FIG. 7E having the same effect (in the latter case, the second gas ScG is introduced upwardly to the crossing part), and alternatively, the circular type and a pair of semi-circles type, as shown in FIGS. 7C and 7D, respectively.

It is preferable to choose a suitable combination of the vertical separator plate and the gas-distributor tube. Recommended combinations are: FIG. 6A and FIG. 7A, FIG. 6B and FIG. 7B or 7E, and FIG. 6C and FIG. 7C or 7D.

Figure 8A:
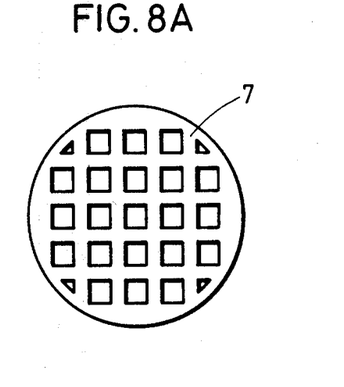
FIGS. 8A and 8B show embodiments of the gas-dispersing board other than that of FIG. 3.
Figure 8B:
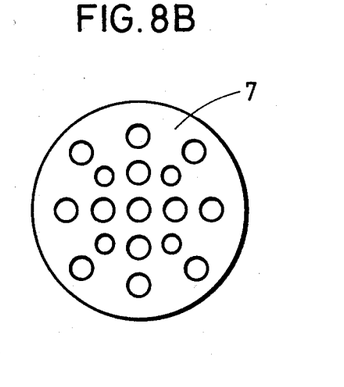

The gas-dispersing plate 7 may include various embodiments. The examples in addition to that shown in FIG. 3 are: the lattice as shown in FIG. 8A, and the perforated plate as shown in FIG. 8B. The lattice may be prepared by duplicating two sheets of slit-plates disposed in contact or with a certain distance.

In the case where the reactor contains three or more catalyst beds and where the second and the third gases are introduced for the mixing between the beds, it is recommendable to use the gas-mixing apparatus of the present invention at each space between two beds.

EXAMPLE

Figure 9A:
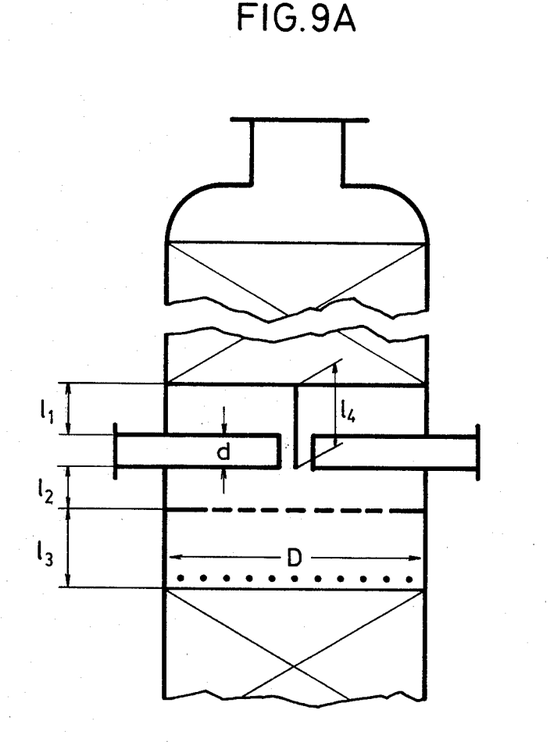
FIGS. 9A and 9B are to explain the dimensional relation between each element composing a reactor according to the present invention.
Figure 9B:
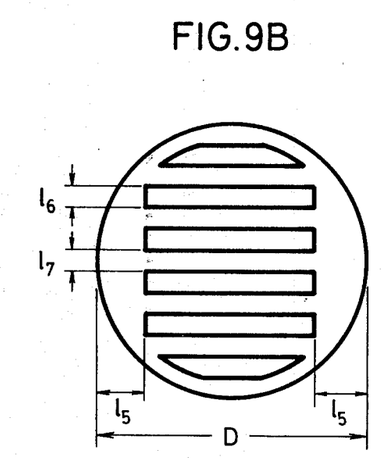

A catalytic reactor of the structure as shown in FIGS. 1 to 3 was constructed with the following dimensions of the parts illustrated in FIGS. 9A and 9B, and each catalyst bed is packed with catalyst.

d=0.084 D
$l_1$=0.14 D  $l_2$=0.022 D  $l_3$=0.182 D
$l_4$=0.224 D  $l_5$=0.17 D  $l_6$=0.042 D
$l_7$=0.028 D

The opening area ratio of the gas-dispersing plate is 48%.

The first gas PrG was prepared by adding methane to air to the methane content of 500 ppm, which gas was introduced from the top of the reactor at the velocity of 0.40 or 0.77 m/sec. The second gas ScG which is just air was blown in through the gas-distributor tube at the velocity of 46.5 or 63 m/sec. The volume ratio of the first gas to the second gas was 10 to 8.

Figure 10:
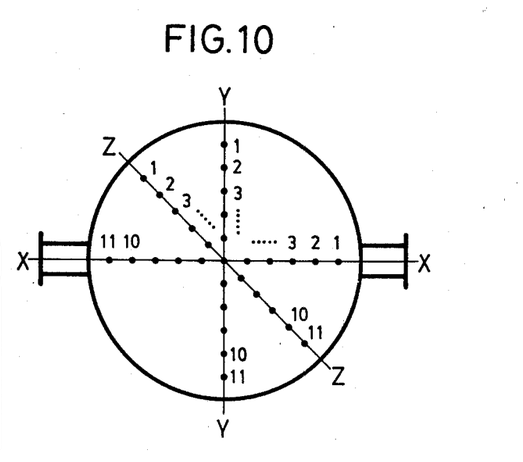
FIG. 10 show the sampling points at which methane concentration is measured to determine the mixing effect of methane-air mixture (the first gas) and air (the second gas) in an embodiment of the present invention.

In order to determine the state of mixing of these gases, gas samples were taken at the upper surface of the second catalyst bed, and the methane contents thereof were measured. The measurements were made (or gas samples were taken) at the points along the three axes rows, X—X, Y—Y and Z—Z as shown in FIG. 10, each 11 points on the axes.

Figure 12:
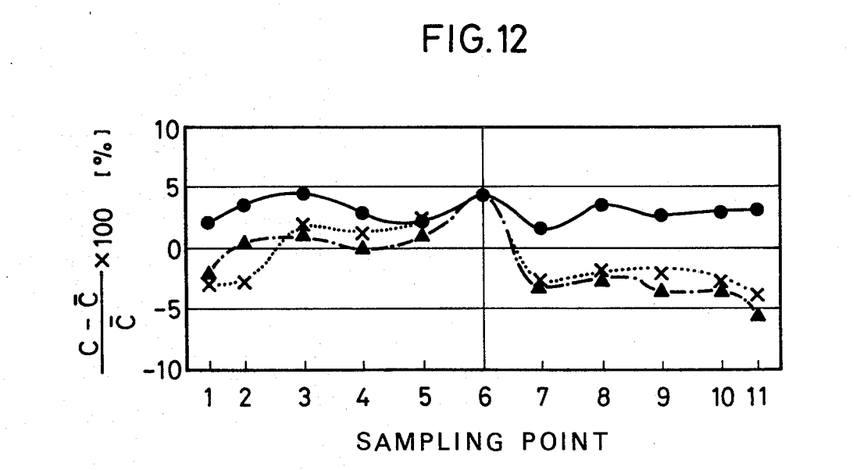
FIG. 12, the data obtained in the reactor according to the invention.

Then, deviations of the measured methane concentration at each sampling point from the average methane concentration were calculated, and the results were shown in FIG. 12.

For the comparative study, the same experiments were carried out as to the cases:

A—where none of the vertical separator plate, gas-distributor tube and the gas-dispersing plate were used;

B—where only the gas-distributor tube was used, and both the vertical separator plate and the gas-dispersing plate were omitted; and C—where the gas-distributor tube and the gas-dispersing plate were used without the vertical separator plate.

Figure 11A:
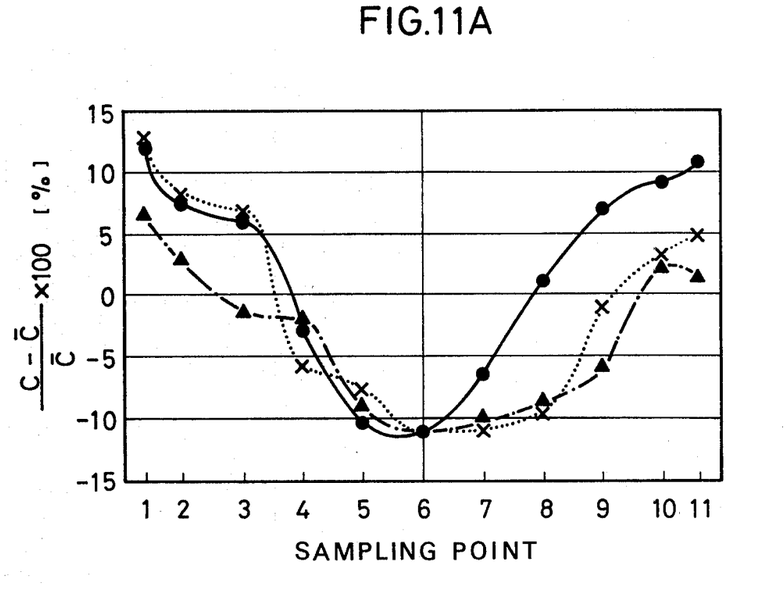
FIGS. 11A, 11B and 11C show the comparative data obtained in a conventional reactor without the gas-mixing apparatus of the present invention.
Figure 11B:
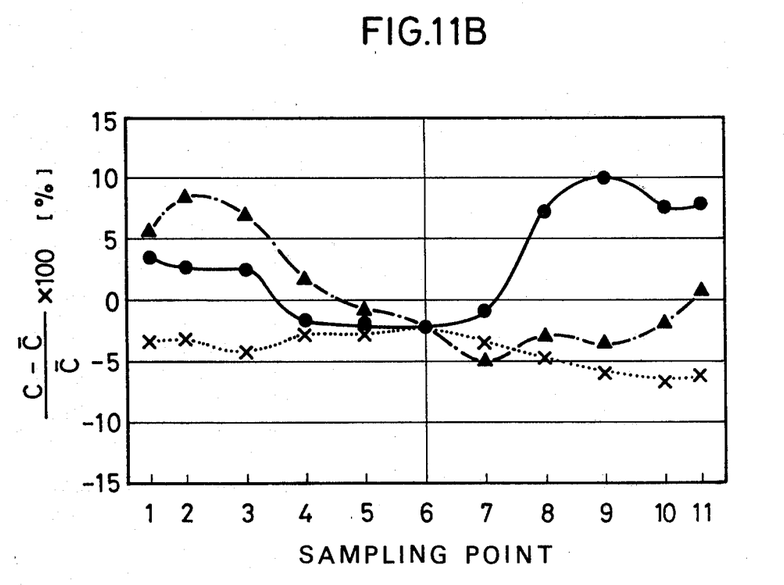
Figure 11C:
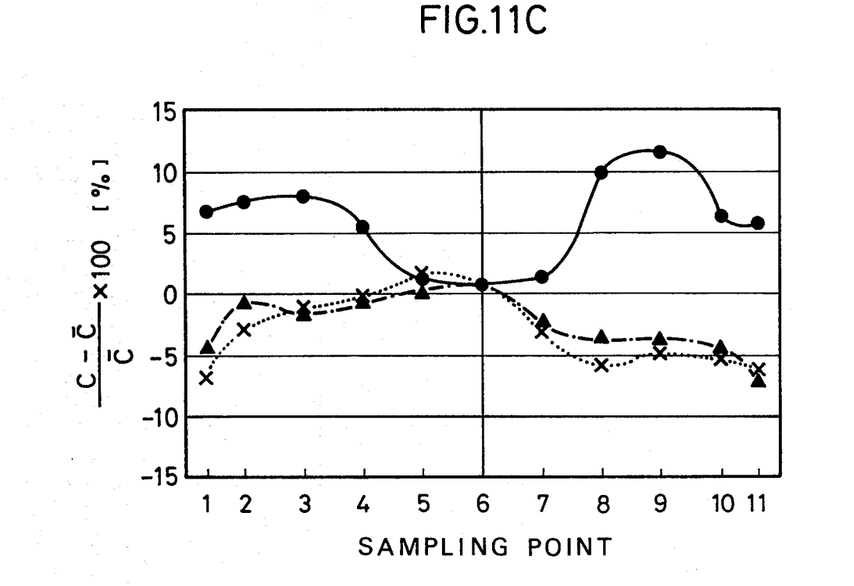

The deviations of the methane concentration from the mean concentration of methane were calculated in the same manner. The graphs showing the data are given in FIGS. 11A, 11B, and 11C.

From comparison of the data in FIGS. 11A, 11B, 11C and FIG. 12, it is clearly understood that the range of deviation of the methane concentrations at the points of sampling is smaller in the catalytic reactor of the present invention, and accordingly, that the mixing of gases is satisfactorily performed.

We claim:

1. A catalytic reactor including
a vessel having an inner diameter and a top,
a plurality of catalyst beds supported in the vessel, each having an upper surface and a bottom,
a plurality of gratings fixed in the vessel, each supporting the bottom of one of the beds,
a first gas inlet at the top of the vessel for introducing a first gas downwardly through the beds,
a second gas inlet for introducing a second gas to a space between two of the beds to be mixed with the first gas, and
a gas mixing apparatus comprising:
at least one vertical separator plate vertically mounted in said space on the downstream face of the grating supporting the upstream bed,
a second gas-distributor tube connected to the second gas inlet, the gas-distributor tube being mounted in said space below the separator plate and having multiple nozzles therein, and
a gas-dispersing plate having multiple openings and being mounted in said space below the gas-distributor tube a certain distance above the upper surface of the downstream bed, the height of a first mixing zone being formed between or corresponding to the space between the bottom of the upstream catalyst bed and the axis of the second gas-distributor tube being at least 0.18 times the inner diameter of the vessel, and the height of the vertical separator plate being at least ½ of the height of the first mixing zone whereby substantially uniform mixing of the first and second gases results across the entire diameter of the vessel.

2. A catalytic reactor according to claim 1, wherein the height of a second mixing zone being formed between the axis of the second gas-distributor tube and the gas-dispersing plate is at least 0.06 times the inner diameter of the vessel.

3. A catalytic reactor according to claim 1, wherein the height of a third mixing zone being formed between the gas-dispersing plate and the upper surface of the downstream catalyst bed is at least 0.12 times the inner diameter of the vessel.

4. A catalytic reactor including
a vessel having an inner diameter and a top,
a plurality of catalyst beds supported in the vessel, each having an upper surface and a bottom,
a plurality of gratings fixed in the vessel, each supporting the bottom of one of the beds,
a first gas inlet at the top of the vessel for introducing a first gas downwardly through the beds,
a second gas inlet for introducing a second gas to a space between two of the beds to be mixed with the first gas, and
a gas mixing apparatus comprising:
at least one vertical separator plate vertically mounted in said space on the downstream face of the grating supporting upstream bed,
a second gas-distributor tube connected to the second gas inlet, the gas-distributor tube being mounted in said space below the separator plate and having multiple nozzles therein, and
a gas-dispersing plate having multiple openings and being mounted in said space below the gas-distributor tube a certain distance above the upper surface of the downstream bed, the height of a first mixing zone being formed between the bottom of the upstream catalyst bed and the axis of the second gas-distributor tube is at least 0.18 times the inner diameter of the vessel, and the height of the vertical separator plate is at least ½ the height of the first mixing zone; the height of a second mixing zone being formed between the axis of the second gas-distributor tube and the gas-dispersing plate is at least 0.06 times the inner diameter of the vessel; and the height of a third mixing zone being formed between the gas-dispersing plate and the upper surface of the downstream catalyst bed is at least 0.12 times the inner diameter of the vessel whereby substantially uniform mixing of the first and second gases results across the entire diameter of the vessel.

5. A catalytic reactor according to claim 4, wherein the nozzles of the second gas-distributor tube are directed so as to blow out the gas in the angle range of 90° to 135° counter-currently to the stream of the first gas, and the second gas-distributor tubes are installed in each segment formed by plural vertical separator plates in the first mixing zone, and the location, the number and the diameter of the nozzles are chosen in such a manner that the second gas may be distributed in the amount proportional to the sectional area of the segments.

6. A catalytic reactor according to claim 4, wherein the opening area ratio of the gas-dispersing plate is from 35 to 60%.

7. A catalytic reactor according to claim 4, wherein the gas-dispersing plate has multiple slits, and the longitudinal direction of the slits is substantially parallel to an axis of the second gas-distributor tube.

8. A catalytic reactor according to claim 7, wherein the slitted gas-dispersing plate has a semi-circular non-opening area at the location just under the fixing part of the second gas-distributor tube to the vessel.

9. A catalytic reactor according to any one of claims 4, 5, 6, or 8 wherein the catalyst beds are three or more, and the vertical separator plates, the second gas-distributor tubes and the gas-dispersing plate are installed in each space between the catalyst beds.

* * * * *